United States Patent
Godik et al.

(10) Patent No.: US 6,587,578 B2
(45) Date of Patent: *Jul. 1, 2003

(54) DYNAMIC-FUNCTIONAL IMAGING OF BIOLOGICAL OBJECTS USING A NON-RIGID OBJECT HOLDER

(75) Inventors: Eduard E. Godik, Suffern, NY (US); Alan Rego, Woodbury, CT (US); Ivan Masyukov, Westwood, NJ (US)

(73) Assignee: Dobi Medical Systems, Inc., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/873,855

(22) Filed: Jun. 4, 2001

(65) Prior Publication Data

US 2002/0032373 A1 Mar. 14, 2002

Related U.S. Application Data

(63) Continuation-in-part of application No. 09/399,306, filed on Sep. 20, 1999, now Pat. No. 6,243,484, which is a continuation of application No. PCT/US98/05559, filed on Mar. 20, 1998.
(60) Provisional application No. 60/041,034, filed on Mar. 21, 1997.

(51) Int. Cl.⁷ ................................................ G06K 9/00
(52) U.S. Cl. ..................... 382/128; 128/109.1; 378/195
(58) Field of Search ................. 382/100, 128, 382/129–134; 378/195; 128/109.1, 95.1, 111.1, 117.1, 125.1; 250/491.1; 600/429, 473, 300

(56) References Cited

U.S. PATENT DOCUMENTS

| | | |
|---|---|---|
| 4,691,333 A | 9/1987 | Gabriele et al. .............. 378/37 |
| 4,943,522 A | 7/1990 | Eisinger et al. ................. 435/7 |
| 4,998,270 A | 3/1991 | Scheid et al. ................ 378/155 |
| 5,204,253 A | 4/1993 | Sanford et al. ........... 435/172.3 |
| 5,257,956 A | 11/1993 | Ewen ............................. 450/1 |
| 5,289,520 A | 2/1994 | Pellegrino et al. ............ 378/37 |
| 5,305,365 A | 4/1994 | Coe ............................. 378/37 |
| 5,347,656 A | 9/1994 | Fabritz et al. .................... 2/67 |
| 5,348,018 A | 9/1994 | Alfano et al. ................ 128/665 |
| 5,349,954 A | 9/1994 | Tiemann et al. ............. 128/634 |
| 5,467,767 A | 11/1995 | Alfano et al. ................ 128/665 |
| 5,474,072 A | 12/1995 | Shmulewitz ........... 128/660.09 |
| 5,499,989 A | 3/1996 | LaBash ...................... 606/130 |
| 5,553,111 A | 9/1996 | Moore et al. ................. 378/37 |
| 6,243,484 B1 | 6/2001 | Godik ........................ 328/128 |

*Primary Examiner*—Jayanti K. Patel
(74) *Attorney, Agent, or Firm*—Perkins, Smith & Cohen, LLP; Jacob N. Erlich; Jerry Cohen

(57) ABSTRACT

A non-rigid object holder unit for use in examination of an object, the unit having a base support, a member movably mounted with respect to the base support to accommodate various sized object. A removable resilient membrane is attached to the first member forming an inflatable component for holding the object to be examined between the inflatable component and the base support. A pressure system operably connected to the inflatable component for controllably inflating the inflatable component. A source of electromagnetic radiation optically associated with the base support and inflatable component for providing a beam of light to the object and an optical detecting system optically aligned with the source of electromagnetic radiation for receiving the electromagnetic radiation passing through and/ or being backscattered from the object. In addition, both the base support and member containing the inflatable component are movable together to accommodate various sized patients.

20 Claims, 7 Drawing Sheets

DYNAMIC-FUNCTIONAL IMAGING OF BIOLOGICAL OBJECTS USING A NON-RIGID OBJECT HOLDER

CROSS REFERENCE TO RELATED APPLICATIONS

This application is a continuation-in-part of copending U.S. patent application Ser. No. 09/399,306 entitled "Dynamic-Functional Image of Biological Objects Using a Non-Rigid Object Holder" filed Sep. 20, 1999 now U.S. Pat. No. 6,243,484 which in turn is a continuation of PCT Application No. PCT/US98/05559, filed Mar. 20, 1998, entitled, "Dynamic-Functional Imaging of Biological Objects Using a Non-Rigid Object Holder." PCT Application No. PCT/US98/05559 application also claims priority of Provisional Application Ser. No. 60/041,034 filed Mar. 21, 1997 entitled "Dynamic-Functional Imaging of Biological Objects Using a Non-Rigid Object Holder." All of the above being incorporated herein by reference.

FIELD OF THE INVENTION

This invention relates generally to dynamic functional imaging of biological objects and, more particularly, to the utilization of a non-rigid object holder in conjunction therewith, and, even more specifically, for use in the screening for breast cancer.

BACKGROUND OF THE INVENTION

One of the largest health problems facing the public today relates to cancer and devising safe and accurate screening procedures especially for breast cancer. There is a substantial difference between breast cancer diagnostics and breast cancer screening, in that breast cancer diagnostics are applied when a patient appears in a doctor's office or hospital with an already existing breast problem. Breast cancer screening relates to cancer detection prior to symptoms occurring. It is hoped with a proper breast cancer screening program that the treatment of breast cancer and potential breast cancer can take place at an early stage and, therefore, effect a high cure rate.

One of the common breast cancer screening procedures in use today involves the use of X-ray radiation during mammography as well as during breast cancer diagnostics with the utilization of stereotaxic mammography which is utilized to localize the pathology, and simultaneously perform a needle biopsy in conjunction therewith to identify the malignancy. Such screening and diagnostic techniques, based on revealing of morphological changes in the breast, many times comes about too late for appropriate treatment, is expensive to perform and in many instances is harmful to the patient by exposing them to X-ray radiation. Furthermore, since the diagnosis obtained through mammography results in a high rate of false positive diagnoses, approximately five times as many patients are exposed to unnecessary X-ray radiation than necessary.

An additional problem for the mammography application to breast cancer screening is the strong compression (up to 30 psi) of the breast between two rigid plates (holder) to immobilize the breast during examination to decrease x-ray scattering in breast tissue. This compression creates substantial discomfort as well as pain for the patient and may even be harmful since there is a danger of cancerous cells disseminating if a lesion is disrupted. In addition to this disadvantage of current techniques, the X-ray radiation itself may be harmful to the patient. Furthermore, another disadvantage of current mammography techniques is that the X-ray radiation can reveal only morphological contrast.

Effective breast cancer screening should be safe and highly accurate in detecting cancers, and should be started from puberty. The procedure should be inexpensive and digital in operation so that comparison between personal results of multiple sequential examinations would be possible. To date, extensive use of such safe breast cancer screening procedures is not a practicality. In Another technique under development today involves optical mammoscopy with spectroscopy which investigates definite changes produced by cancer in the physiological patterns of tissues, dominantly in the steady state distributions of blood content, oxygenation and metabolic rate. This technique, however, is directed dominantly to achieving as high spatial resolution as in that in morphological imaging. The utilization of lasers to overcome strong multiple scattering of light in the biological tissues makes such a technique rather expensive and questionably safe for screening.

The present assignee has developed a dynamic functional imaging technique of the type described in U.S. Pat. Nos. 5,865,167 and 5,747,789; and more specifically to an optical functional mammoscopy technique as described in U.S. Pat. No. 5,730,133. In such a technique, more specifically denoted as dynamic functional optical marmoscopy (DFOM), near infrared radiation in the wave length range of 0.6–1.1 microns is utilized. This near infrared radiation is very similar to regular background illumination and, therefore, eliminates many of the problems associated with past devices which rely upon lasers. Further, the intensity applied (10–30 mW/cm) is comparable with that of background thermal infrared radiation. Consequently, the utilization of DFOM is absolutely safe. Further, this technique applies the transient functional patterns of tissues with the pixels being temporal signatures of spontaneous tissue functioning and reactivities in response to selected stimuli which are reflective of a whole organ's synergy. Such an approach is extremely effective for the examination of mammary glands or breasts characterized by high symmetrical physiological functioning and structure, biologically directed to the nipple. In this case, temporal sequences of optical images are recorded. To obtain the specificity of the temporal signatures necessary for pathology transient pattern recognition, the interframe intervals should be differentially small against the time constant of the physiological process One drawback to such a dynamic functional optical mammoscopy technique is the utilization to date of hard or rigid holders therewith. The same difficulties encountered by the use of such rigid holders in past techniques also constitute a problem when utilized with the dynamic functional optical mammoscopy technique. It is therefore necessary to develop in conjunction with such a dynamic functional optical imaging system a holder which can form an integral part thereof, be reliable in obtaining accurate results and overcome the problems associated with past holders.

It is, therefore, an object of this invention to provide a dynamic functional optical imaging system which can be utilized in conjunction with the study of biological objects and utilizing a non-rigid object holder therewith.

It is another object of this invention to provide a non-rigid holder for use in medical procedures, especially breast examinations.

It is the further object of this invention to provide a dynamic functional optical imaging mammoscopy system which overcomes the problems of past cancer diagnostic and screening techniques.

SUMMARY OF THE INVENTION

The objects set forth above as well as further and other objects and advantages of the present invention are achieved by the embodiments of the invention described hereinbelow.

The present invention incorporates a non-rigid biological object holder within a dynamic functional imaging system, and, in particular, a dynamic functional mammoscopy system which is capable of performing accurate breast cancer screening. It should be realized, however, that this holder is not limited to use as only a breast holder and may be used, for example with other parts of the body such as the abdomen, muscles or even an entire body as in the case of an infant or other biological objects. Within the system of this invention, a biological object such as the breast can be placed between one or more flexible, elastic, resilient membranes that form parts of an inflatable bag system. A single flexible, elastic, resilient member (soft holder) is used with the preferred embodiment for the present invention. The examination takes place under controlled external pressure and thereby overcomes many of the problems associated with past hard plate holders as used in mammography or optical mammoscopy systems. The external pressure control together with the optical system of the dynamic functional imaging system operates in a synergistic fashion with the non-rigid holders of the present invention.

The design of the present invention, made up of a number of different embodiments including but not limited to three way adjustability features as well as the removability of the resilient membrane (soft holder), overcomes the problems associated with past breast cancer screening techniques, examples of which are described above, and enables the breast cancer screening technique to take place in a safe, inexpensive and highly accurate manner.

DETAILED DESCRIPTION OF THE PREFERRED EMBODIMENTS

Figure 1:
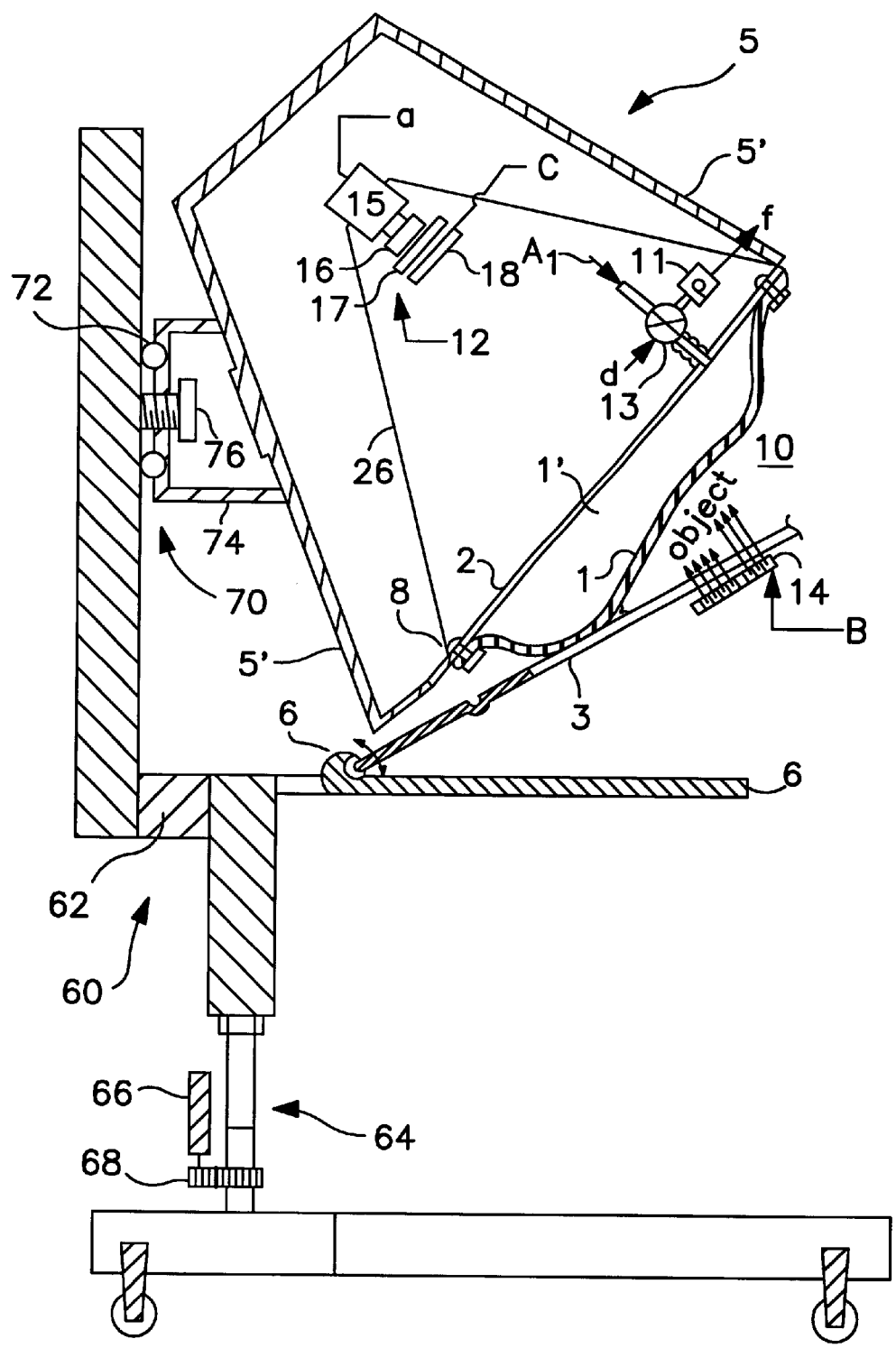
FIG. 1 is a schematic representation, illustrating a side view partially in cross-section, of the dynamic functional mammoscopy system of this invention incorporating therein the non-rigid holder of this invention.
Figure 2:
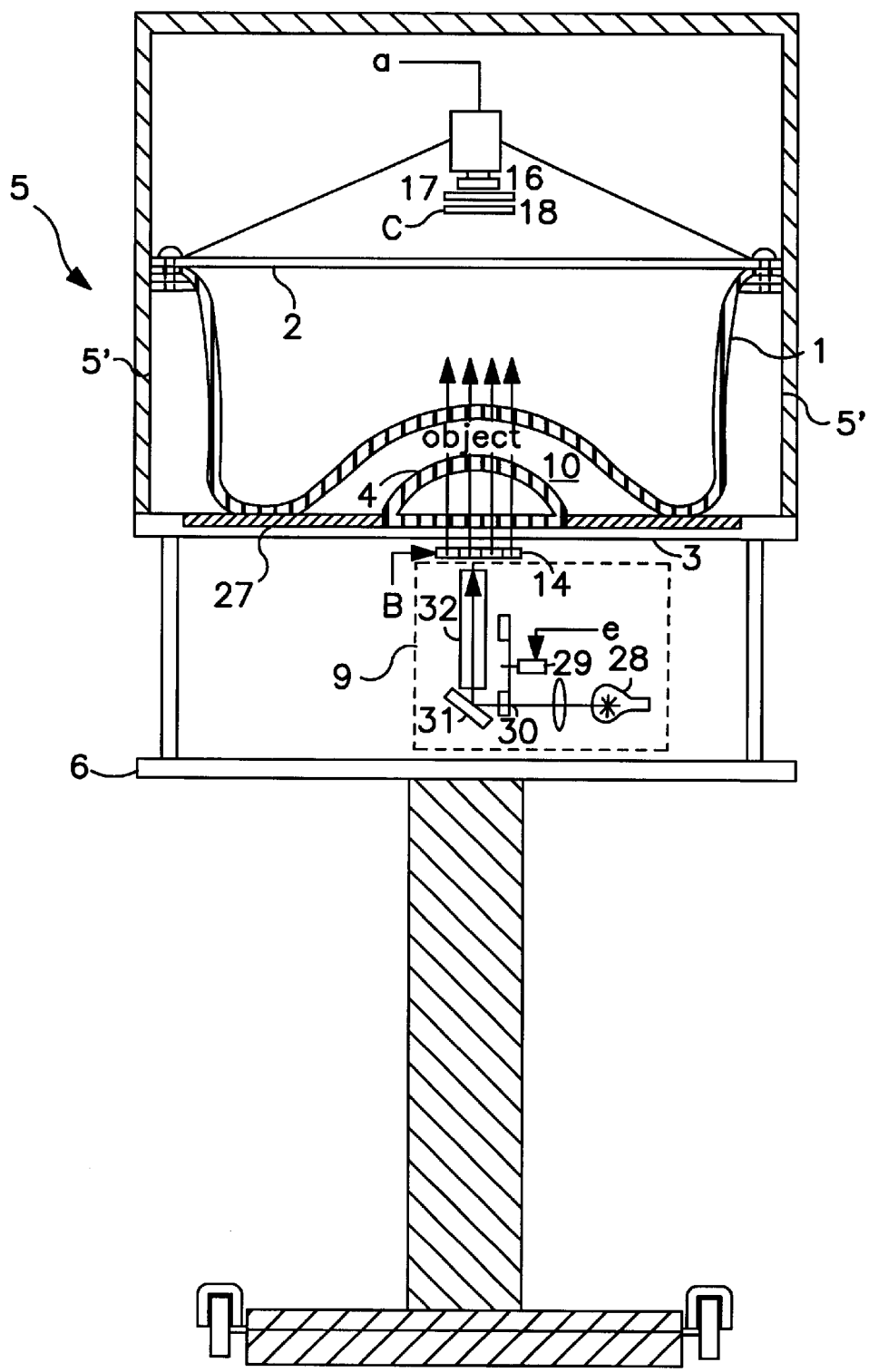
FIG. 2 is a schematic representation, illustrating a front view partially in cross-section, of the dynamic functional mammoscopy system of this invention shown in FIG. 1 incorporating therein the non-rigid holder of this invention and also showing an alternate illumination system in the dashed box.
Figure 3:
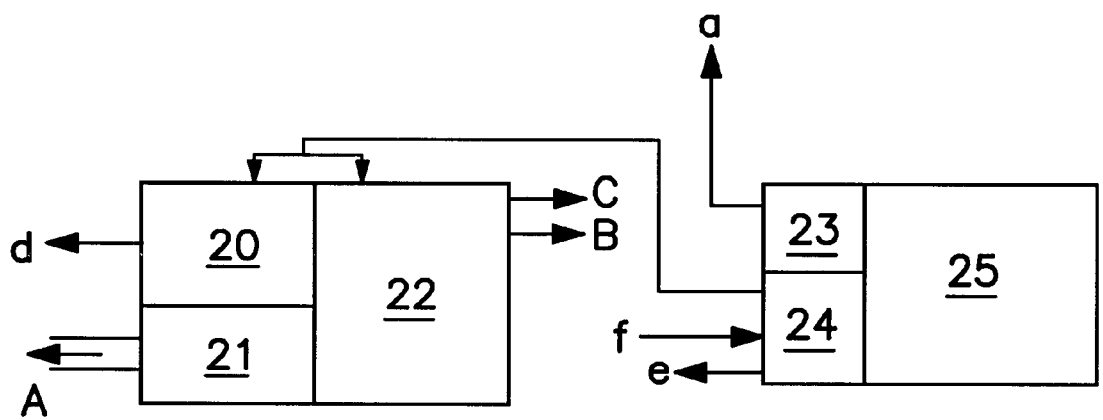
FIG. 3 is a block diagram of the major electronic components of the dynamic functional mammoscopy system of this invention.

The apparatus making up a dynamic functional optical mammoscopy (DFOM) system with the non-rigid or soft holder incorporated therein is described with respect to FIGS. 1–3. Reference can be made to the above cited U.S. Pat. Nos. 5,865,167 , 5,747,789 and 5,730,133 for a basic understanding of dynamic functional imaging systems and its use in mammoscopy. These patents, all commonly owned by assignee, are not to be construed as a limitation on thsis invention and are incorporated herein by reference. Furthermore, for purposes of clarity, like references numerals will be used throughout the description and drawings to refer to substantially identical components.

With the present invention, and referring to FIGS. 1 and 2 of the drawings, the object or breast 10 under examination is softly compressed between preferably a single the non-rigid, elastic, resilient membrane 1 (considered the soft holder) attached to transparent plate 2, preferably made of Plexiglas® to create an inflatable bag 1'. As shown in FIG. 2, the membrane 1 is framed by a housing made up of nontransparent members or plates 5' which enable adjustment therof with respect to base support 3. This type of non-rigid holder substantially eliminates any discomfort to the patient during examination as previously encountered with the rigid holders necessitated by prior mammography procedures.

It is possible with the present invention to examine each breast individually with a single non-rigid holder unit or, to utilize a pair of such units and associated components in a manner similar to that described in U.S. Pat. No. 5,730,133. It should be further realized that the holders may also be configured to hold other parts of the body (biological objects) or even an entire body as in the case of an infant. A near-infrared (NIR) light source 14 transilluminates the object (the breast 10) and the bag 1' covering the breast. The optical recording system 12 includes a CCD camera 15 (with lens 16) and dynamic interface board (frame grabber) 23 for acquisition of the sequences of the optical frames for transmission to a conventional computer 25, which may be a personal computer (PC). As shown in FIG. 3, the computer 25 via PC interface board 24 and the pneumatic unit 20 controls the pressures created by compressor 21 in bag 1' and via electronic interface unit 22 controls the illumination conditions created by the illuminator or light source 14. The recording system 12 is utilized for measuring and analyzing relative spatial-temporal variations of the intensity of the light passed through the breast 10 due to the modulation of the optical parameters (absorbance and scattering) of the breast tissues by its physiological functioning (blood, oxygenation and metabolic rate redistribution). An imaging platform system 60 is adjustable to allow the imaging platform 62 to raised and lowered to accommodate different sized people by means of a movement system 64 comprised of a conventional motor 66 and gears 68. The camera 15 can be moved in relationship to base support 3 by means of a mechanical rail system 70 made up of componenets 72 and 74 used in conjunction with break or locking system 76. This allows the user to fix the relationship between housing 5 and base support 3. These two adjustment features of the invention permit both adustability of the holder unit for the size of the patient as well as the patient's breast size. In order to formulate continuous temporal sequences of the optical images, they are recorded at intervals differentially small as compared with time constants of the tissues physiological dynamics, that is, several frames per second is a sufficient rate. The frames sequences are accumulated in the computer memory. The relative temporal variation of the intensity, that is, the temporal signature (TS) is calculated two ways: 1) by subtracting the first frame from any sequential one and normalizing the difference on the intensity distribution on the first frame or 2) taking the logarithm of the derivative. To reveal the pathological functional contrast the Functional Segmentation (FS) is applied by various options, including but not limited to, the cross-correlation of the FS over the image. As mentioned above, the soft holder of this invention is substantially more effective than past holders for examination of functional physiological parameters of soft tissues since it is the pressure applied to the object under examination that controls the tissues' hemodynamics, and thereby, such related parameters as tissue elasticity, oxygenation, metabolic rate, skin perspiration, etc. Furthermore, since the soft holder of this invention is naturally compatible with soft tissue and does not create pain or any discomfort for patients it is a substantial advancement over past holders used in breast examination.

The most effective application of soft holder of this invention is in breast examination with the dynamic functional optical imaging (DFOI) in a transillumination or reflectometry scheme. The soft holder is also applicable for dynamic functional imaging of the abdominal cavity (in reflectometry scheme) and muscles (both transillumination and reflectometry schemes). The present soft holder can also be utilized for gentle immobilization during DFOI examination of the brain, abdomen, and even the whole body of newborns in baby-incubators.

Referring once again to FIGS. 1 and 2 of the drawings, a silicone film with a thickness of 30–150 μm is preferred for the elastic, flexible membrane 1. Such silicone being stretched and thereby made thinner after inflation of the bag 1' so as to become sufficiently transparent for the functional imaging to take place when the spatial resolution is not so critical. In fact, the stretched silicone interferes no more with the light propagation than the diffusive thin layer of the skin. Thicker silicone film having a thickness of approximately 100–300 μm, or plastic film (for example, polyethylene film with thickness of 20–50 μm) can also be used.

Figure 6:
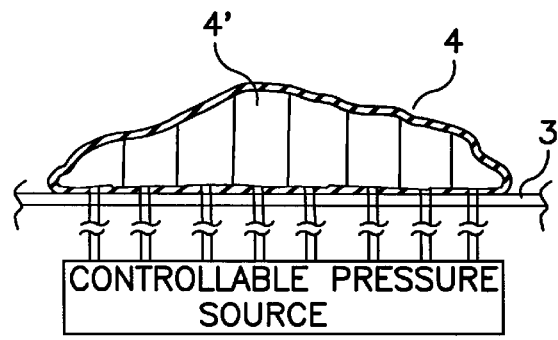
FIG. 6 is a cross sectional view of a resilient membrane having compartments therein to more controllably regulate pressure.

As shown in FIG. 6 of the drawings, the bag 1' can be made from several sections of material thereby even further controlling compression. This gives rise to the possibility of selectively compressing portions of the breast or object in order to control the distribution of thickness of the breast or other object under investigation or to equalize the thickness of the breast being compressed in the soft holder. It is especially useful to concentrate compression of the breast adjacent the area of pathology. Equalization of the thickness of the object (breast) directly results in effecting the intensity of the light passing through the object, which is important for the necessary expansion of the dynamic range of the recording system, as described below. It should be further noted that the housing for the soft holder can be rotated in order to pass light through the breast in any direction. In addition, the membrane can not only be made of silicone, but also any other suitable transparent film such as polyethylene, latex.

Prior to the examination process, the illumination platform 62 is moved into place to accommodate the patient. The object, preferably a breast 10 is placed on the illumination plate or base support 3 such that the chest wall comes in contact therewith. Base support 3 may also be adjustable about a pivot point 7 (optional) with an optimum breast positioning angle between support base 3 lower support 6 of platform 62 being approximately 20–30 degrees. The imaging system 26 is moved into place so the the substantially uninflated membrane 1 comes in contact with the breast item 10. Thereafter, the breast is covered by the silicone membrane 1 of bag 1' which is inflated up to an initial pressure of approximately 2–5 mm Hg. Once in position housing 5 can be secured in place with clamping mechanism 76. Pressure in the bag 1' is increased up to 5–10 mm Hg just before the start of the breast examination. During examination, bag 1' is inflated in a controlled fashion by control valve 13 under pressuremeters 11 which monitor the operation.

The soft holder unit of this invention, with elastic, resilient membrane 1 is an active and interactive part of both the DFOM method and apparatus of the present invention as described below. During the initial part of the examination a smooth compression of the breast takes place by slow inflation (0.5–2 mm Hg/sec) of the bag 1' from the initial pressure of 5–10 mmHg up to approximately 10–60 mm Hg (this pressure being more than one order of magnitude less than level of the pressure applied in mammography). The temporal valuation of the optical image during this procedure reveal differences (the contrast) in the tissues' compressibility. The less compressible (palpable) area decreases less of the thickness and so there is less of an increase of the transparency during the compression. In nonpalpable cases another mechanism, that is, the difference in the tissues mechanical impedance determined by the condition of physiological liquids (blood and lymph), that is, venular and lymphatic resistivity against blood and lymph repulsion can reveal the pathology. Another possible scenario would be to increase the pressure rapidly, for example, 3–10 mm Hg for one second and just thereafter investigate tissue reaction during approximately 20–40 seconds at the same increased pressure. Such a procedure creates a dynamic contrast between pathological and normal tissues. It is also possible to combine several sequential pressure steps up, for example, four steps up of approximately 3–7 mm Hg/sec each, starting from initial level of 5–10 mm Hg, with a duration of the pressure plateau 30–40 sec between the steps to investigate the image valuation. Other alternate steps can also be applied. The period of the pressure variation described above is close to that of spontaneous oscillations of blood content into the breast so it is possible to synchronize the external pressure variations with this internal oscillation in real time based upon feedback from the changes in light intensity. Such interactive procedure substantially increases the possibility to reveal the pathology.

The pressure protocol can also include an investigation of the DFOM-image evaluation after one or more pressure increases or jumps, or after completion of the final pressure jump or increase, that is when the pressure is stabilized for 3–10 minutes at a "pressure plateau." During the plateau phase, under constant pressure, evaluation is performed at the constant pressure in order to determine possible contrast in long term tissue reactivity. After the above investigation or evaluation has taken place, the constant or pressure plateau can be decreased by sequential downward steps or jumps, a single decrease in pressure or a sequence of pressure drops until the initial pressure of 5–10 mmHg has been reached. Thereafter a sequential investigation or evaluation can take place at the 5–10 mmHg pressure level for 3–10 minutes to reveal any possible contrast in long term tissue relaxation.

Besides the external pressure tests conducted with the silicone membrane 1 described above, other stimuli can be utilized such as hypoxy, hypercopny, glucose uptake and especially sensory tests from the nipple (the main sensory area of the breast). The image valuation after such tests in the soft holder will include two modalities. It is possible to see from the basic analysis presented below that the relative variation of the intensity passing throughout the breast in the soft holder $\Delta I/I(x,y,t,\lambda)$ is equal to $$\Delta I/I(x,y,t,\lambda) \cong K \times D(\Delta K/K + \Delta D/D)$$

where (x,y) are coordinates of the pixel, t represents time, $\lambda$ represents wavelength of the light, D represents the thickness of the compressed breast, K, the light attenuation coefficient in multiple scattering media is equal to the square root of (3 Ks×Ka), where Ks is light scattering coefficient, Ka is the absorbance coefficient. The first contribution, $\Delta K/K$ reflects the modulation of the tissues optical parameters by blood and oxygenation changes initiated by the tests directly. The second contribution, $\Delta D/D$, reflects differential variations of the breast volume and shape due to redistribution of the blood and lymph in the breast initiated by the tests.

It is also important to realize that utilization of the non-rigid holder of this invention opens up the possibility of further pathology projection. For example, the relative temporal variations of the light intensity transmitted through the object such as the breast $\Delta I/I$ (x,y,t) are proportional to the variations of the light attenuation by the breast tissues $\Delta(K \times D)$, where K(x,y,t) is the tissues attenuation coefficient, combining the scattering and the absorption, and D(x,y,t) is the thickness of the breast;

$\Delta(K \times D)$ consists of the two contributors $\Delta K \times D$ and $\Delta D \times K$: the first one is responsible for the conventional optical diffusion projection and the additional second one represents a new opportunity—dynamic optical deformoscopy (DOD). DOD contrasts the pathology based on the differences in the dynamical compressibility of the tissue. It is, in actuality, the mechanical projection of the pathology from the tissue's depth so the spatial resolution is not restricted by light diffusion. This new, additional modality of the DFOM is similar to palpation but with the advantages of being objective and, even more importantly, being dynamic imaging modality which reveals not only static masses, but also a dynamical pattern of the tissue's compressibility. This pattern reflects the corresponding dynamic functional pattern of the blood (and lymph) circulation in the mammary gland or object under examination. Such dynamic "palpascopy" opens the possibility of recording data with high accuracy and storing, in a computer memory, dynamic "molds" of the mammary gland, specific to various physiological conditions.

For effecting the above, a coherent laser source and system for projecting some type of interference pattern (grating or grid) on the membrane surface, covering the breast, are necessary. In addition it is necessary to utilize CCD for the recording of dynamical changes of the grating or the grid parameters during breast compression or its spontaneous behavior. Such a procedure and system gives rise to the possibility for the Dynamic Optical Deformascopy of the breast or other part of the body in a reflective mode; the sensitivity being sufficient to record blood redistribution dynamics in the skin as an alternative to the rather expensive infrared thermovision procedure.

By application of an oscillating pressure it is possible to initiate periodic changes of breast deformation $\Delta D(x,y)$, recorded by DOD. This opens the possibility of obtaining distribution of absolute values for the attenuation coefficients K(x,y) for different wavelengths and distribution of the blood volume, and the oxygenation and metabolic rate by recording relative changes of the intensity of light, transil-luminating breast, $\Delta I/I(x,y)$ $K(x,y) \times \Delta D(x,y)$. The periodical variation of deformation lends itself to increased accuracy by intensity synchronous recording.

Figure 8:
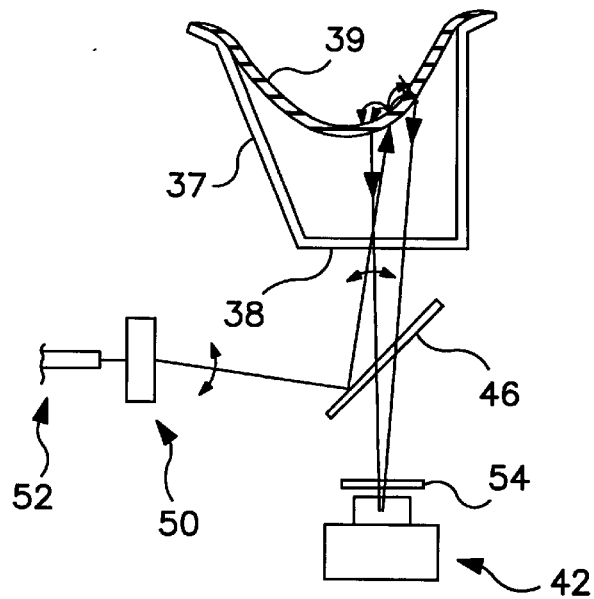
FIG. 8 is a schematic representation of a still further embodiment of the present invention which incorporates a single resilient member and a scanning system.

The present invention also incorporates therein, but is not limited to further embodiments as set forth below. For example, variations in the type of illuminators used, two of which are shown in the drawings. One being the LED array 14 shown in FIG. 1 and the other being illustrated in the dashed box as fiberoptic illuminator 9. In addition, a scanning mechanism as shown in FIG. 8 can also be used.

The LED array 14 can be made up of, for example, several (up to 127) sections whose intensities are independently controlled by electronic unit 22 to equalize the intensity distribution on the first frame before test applications begin. It is necessary to expand the dynamic range of the recording system to get high accuracy. Examples of ranges of four spectral bands picked are at wavelengths of 0.6–0.78 $\mu$m, 0.78–0.82 $\mu$m, 0.82–0.93 $\mu$m, and 0.93–1.2 $\mu$m. The range of 0.6–0.78 $\mu$m is specific for the venular blood absorbance that is much stronger in the cancerous tissues. This band is very sensitive to changes in the tissues oxygenation. The band range of the isobestic point 0.78–0.82 $\mu$m for oxy- and dezoxyhemoglobin absorbance is sensitive only to changes of the blood volume and so it is a good reference for the band 0.6–0.78 $\mu$m and 0.82–0.93 $\mu$m to separate contributions of the blood volume and the oxygenation changes. The band in the range of 0.93–1.2 $\mu$m is sensitive to water content and temperature, those both being increased in cancerous tissues versus normal tissues. For the above purpose, the LED's, with the four wavelengths mentioned, were distributed by groups along the illuminator 14. Similar LED's (one from each group) are switched alternatively to obtain one multispectral frame, the four spectral subframes being recorded sequentially. For example, for the multispectral dynamic imaging with a rate of one frame per second, three different spectral subframes per second should be recorded. The intensity of illumination was set at no greater than 30 m W/cm$^2$/sec to exclude any heating discomfort for the patient. As shown clearly in FIG. 2, a nontransparent diaphragm 27, adjustable to the breast size, was used to protect against leakage of the illuminating light next to the breast.

Use of the alternate fiberoptic illuminator 9 is also shown in FIG. 2 in the dashed box. Fiberoptic illuminator 9 includes a light source such as halogen lamp 28, a filter wheel 29 with alternately changeable filters 30 controlled by PC-board 24 corresponding to the spectral bands explained above, reflective thermofilter 31 and fiberoptic guide 32.

The recording system for the DFOM of this invention, as explained above, obtains maximum accuracy in measuring relative temporal changes of the intensity along the optical image. For this purpose, the CCD with a maximum dynamic range should be utilized. To increase the dynamic range, a CCD with a large size of the pixel, 128×128 pixels are appropriate, since Dynamic Functional Optical Imaging is less reliant on spatial resolution than in morphological imaging. For additional increase of the dynamic range, the intensity in the first frame should be maximally equalized. For this purpose, in addition to equalization by the controlled multisectional illuminator 14 and equalization of the compressed breast thickness by controlled inflation of a multisectional bag 1' If needed and shown in FIG. 6, as were explained above, controlled optical transparency can be obtained by the use of, for example, liquid crystal film 18 for final intensity equalization before the CCD.

It is also important to exclude scattered light, especially its temporal variation, during operation of the system. Therefore, a nontransparent screen 26 with transparent window 2 for the CCD and spectral filter 17 capable of eliminating light with wavelengths of less than 0.6 μm (that cannot pass through the breast) are utilized with the present invention. The membrane 1 is attached to the perimeter of metal frame 26 adjacent the chest wall for breast examination.

Figure 4:
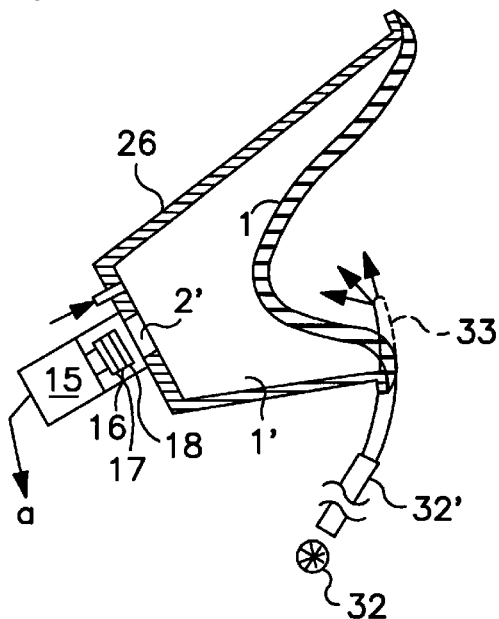
FIGS. 4 and 5 represent the dynamic functional mammoscopy system of this invention incorporating therein alternate embodiments of the non-rigid holder of this invention.
Figure 5:
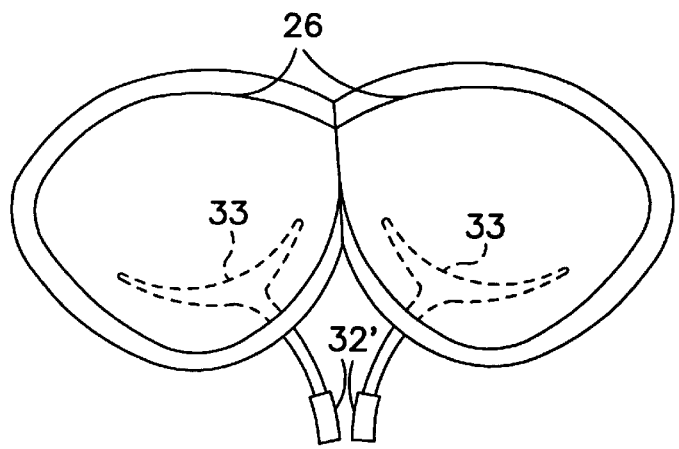

In addition to the above, front view projection is very important for breast examination with the present invention since the breast functioning and morphology are symmetrical around the nipple. The design of the non-rigid or soft holder of this invention for front examination is shown in the embodiments of FIGS. 4 and 5. In this case, the silicone membrane 1 compresses the breast against chest wall of the patient. In order to provide for the possibility of such compression the support 26 should be attached to the chest wall or other part of the body under investigation by any suitable securing means such as a strap or adhesive may be used with the present invention. For illumination, a transparent plastic adapter 33, taken from a set of adapters of different size and shape determined by various breast sizes and shapes, is placed under the breast. The adapter 33 is connected with fiberoptic guide 32' providing light from light source 32 as shown in FIGS. 4 and 5. The optical recording system 12 is similar to the system shown in FIG. 1 and is located adjacent a transparent window 2'.

Figure 7:
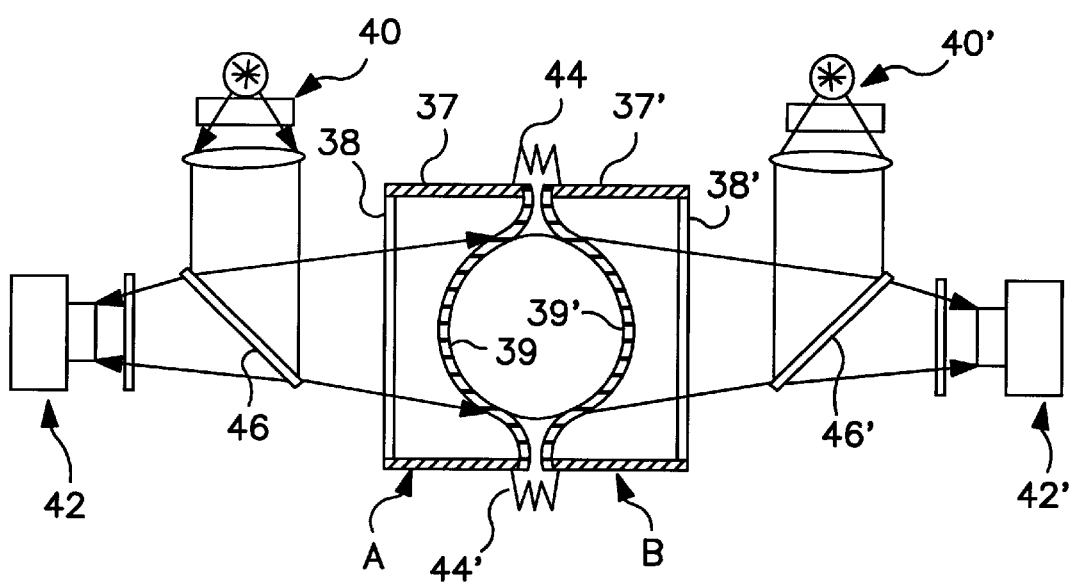
FIG. 7 is a schematic representation of a further embodiment of the present invention which incorporates therein the use of a symmetrical non-rigid holder.

Reference is now made to FIG. 7 of the drawing which illustrate a further embodiment of the present invention showing a symmetrical design of the non-rigid holder of this invention incorporated within a DFOM apparatus. More specifically, in this embodiment, the resilient membranes 39 and 39' are substantially identical and formed of two separate "mirror image" components A and B. These components are made of non-transparent frame portions 37 and 37', respectively, and transparent windows 38 and 38', respectively, to which the resilient membranes 39 and 39' are attached. The transparent windows are in optical alignment with the optical source and detecting systems 40, 40' and 42, 42'. The membranes 39 and 39' are controllably inflated by a pressure system (not shown) similar to the system used for controllably inflating membranes 1 and 4 within FIG. 1 of the drawings.

The non-rigid holder of the type shown in FIG. 7 of the drawings is primarily used with a patient lying down and when the breast symmetry around the nipple is not disturbed by its weight. The two components A and B are held together by flexible members 44 and 44' which enable the frames to be adjustably moved with respect to one another when placed around a breast or other object to be examined. In the embodiment shown in FIG. 7 of the invention, there is a symmetrical disposition of the optical or light sources 40 and 40' and the detecting systems 42 and 42'. This set up enables both sides of the object or breast to be examined simultaneously by alternately (frame by frame) switching of the light sources 40, 40' and detecting systems 42, 42'. The light sources and detecting systems used with this embodiment of the invention are identical in design and incorporates therein similar components as shown with respect to FIG. 1 the drawings. In conjunction therewith, beam directors (partially reflective) 46 and 46' are utilized to both direct and redirect the light source radiation to and from the object under examination. It is clear in this embodiment that the light source(s) and light detector(s) are located on the same side.

Reference is now made to FIG. 8 of the drawings which illustrates an embodiment of the invention which includes a single resilient member 39 attached to a nontransparent frame 37 and a transparent window 38 together with a scanning system 50 for light emission from source 52. The scanning system enables the light source to be in the form of a single source scanned over a preselected area of the breast or object under examination. A detecting system is incorporated within the embodiment of FIG. 8, preferably on the same side of the breast as the source. A partially reflective beam director 36 is utilized therewith as with the embodiment of FIG. 7.

In the reflective mode, the light source is located on the same side and is used to record a radial distribution of intensity around the illuminating beam to obtain the necessary distribution of physiological pigments (blood, oxygen, etc.) over a preselected depth in the illuminated area.

Special optical shielding (shadowing) of the central part of the image before the CCD, that is, the bright illuminated area of the beam impacting the breast surface may be required to exclude overloading of the CCD. A liquid crystal transparent (or other) non-linear filter 54 with inverse transparency dependent on the intensity of the light source can be placed before the CCD 42. The general operation of the embodiments of the invention shown in FIGS. 7 and 8 are similar to those described with reference to the embodiments of FIGS. 1 and 2.

Figure 9:
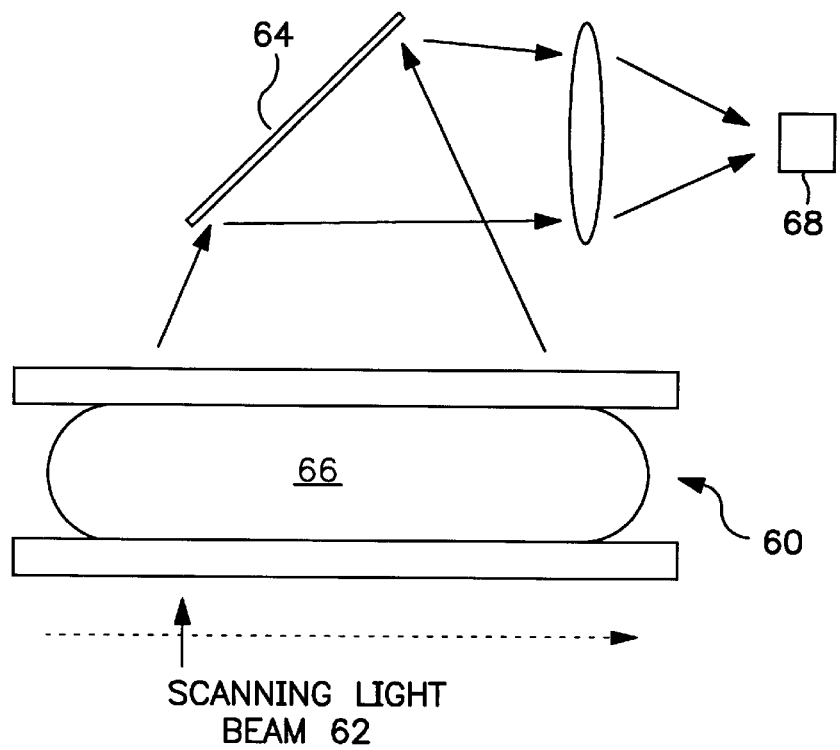
FIG. 9 is a schematic representation of a beam scanning system used with a further embodiment of the present invention.

In the transillumination mode, the non-rigid holder is utilized in combination with a single channel photo detector, placed on the other side of the breast to record integral intensity of the transilluminating light for different locations of the illumination beam. This enables the pathology to be investigated which is located closer to the illuminating side of the breast. Reference is made to FIG. 9 of the drawings for a schematic illustration of such a mammoscopy set up 60 having a scanning light beam 62. A semitransparent mirror 64 enables the combination of a single channel photodetection of integral intensity thransmitted through the breast 66 with the recording of breast images by a CCD camera 68.

Figure 10:
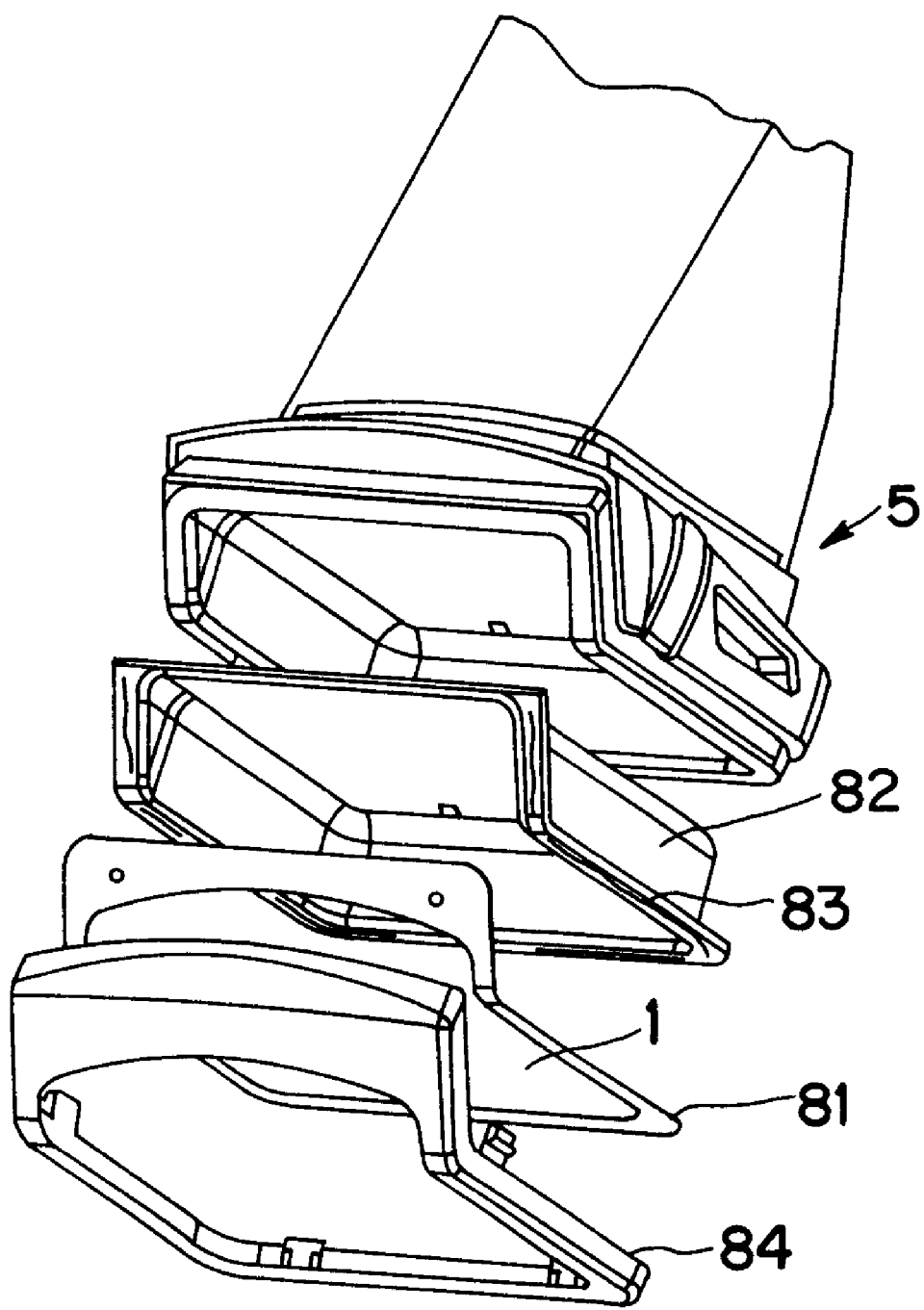
FIG. 10 is an exploded pictorial view of the removable softholder utilized with the present invention.

All embodiments of the invention can also provide for a removability of the elastic, resilient membrane 1. A specific embodiment is shown in exploded fashion in FIG. 10 of the drawings. More specifically, membrane 1 is framed by a housing 81 made preferably of metal, but also, for example of plastic or silicone. A pressure well 82 is mounted in the camera housing 5. Membrane housing 81 connects to the pressure well 82 by any conventiional gasket 83. A camera housing door 84 which traps membrane housing 81 between gasket 83 and door 84. The door 84 provides enough compression force to allow a pressure seal to form.

Although the invention has been described with reference to particular embodiments, it will be understood that this invention is also capable of further and other embodiments within the framework of this invention.

What is claimed is:

1. A non-rigid object holder unit for use in examination of an object, said object holder unit comprising:

a platform assemby;

first and second members movably mounted with respect to each other and said platform assemby;

means operably connected to said first member for controllably moving said first member with respect to said platform assembly and said second member;

a resilient membrane attached to said first member, said resilient membrane forming an inflatable component for holding the object between said inflatable component and said second member;

means operably connected to said inflatable component for controllably inflating said inflatable component;

a source of electromagnetic radiation optically associated said second member for providing a beam of light to the object;

said resilient membrane and portions of said first and second members being transparent to said electromagnetic radiation; and an optical detecting system optically aligned with said source of electromagnetic radiation for receiving said electromagnetic radiation passing through and/or being backscattered from the object.

2. The non-rigid object holder unit as defined in claim 1 wherein said platform assembly is adjustable to accommodate various sized individuals.

3. The non-rigid object holder unit as defined in claim 1 wherein said resilient membrane is removably attached to said first member.

4. The non-rigid object holder unit as defined in claim 3 wherein said platform assembly is adjustable to accommodate various sized individuals.

5. The non-rigid object holder unit as defined in claim 1 wherein said controllably moving means comprises a rail system including a clamping component.

6. The non-rigid object holder unit as defined in claim 1 wherein said resilient membrane is made in sections.

7. The non-rigid object holder unit as defined in claim 1 wherein said source of electromagnetic radiation is located adjacent said second member and said optical detecting system is located adjacent said resilient membrane.

8. The non-rigid object holder unit as defined in claim 1 further comprising means for securing said first and second members in a predetermined position with respect to each other.

9. The non-rigid object holder unit as defined in claim 1 wherein said resilient membrane has a thickness of approximately 30–300 microns.

10. The non-rigid object holder unit as defined in claim 9 further comprising means for controlling the intensities of each LED in said array and wherein said array produces electromagnetic radiation of at least two different spectral bands.

11. The non-rigid object holder unit as defined in claim 10 wherein there are four separate spectral bands of electromagnetic radiation, one being approximately 0.6–0.78 microns, another being 0.78–0.82 microns, another being approximately 0.82–0.93 microns and another being approximately 0.93–1.2 microns.

12. The non-rigid object holder unit as defined in claim 1 wherein said source of electromagnetic radiation is in the form of an LED array.

13. The non-rigid object holder unit as defined in claim 1 wherein said source of electromagnetic radiation is in the form of a fiber optic illuminator.

14. The non-rigid object holder unit as defined in claim 1 wherein said non-rigid object holder unit is in combination with a system for performing dynamic functional imaging of the object.

15. The non-rigid object holder unit as defined in claim 14 wherein the object is a human breast.

16. A method of using a non-rigid holder unit during an examination of an object by dynamic functional imaging, the non-rigid holder unit having a platform assembly, an inflatable component including a resilient membrane and a support member, said method comprising the steps of:

adjusting the platform assembly to accommodate the size of an individual being examined;

adjusting the position of the inflatable component with respect to the support member;

inflating said component to a predetermined pressure; and controllably inflating said component during the examination.

17. The method of using the non-rigid holder unit as defined in claim 16 further comprising the step of gradually inflating said component during the initial part of the examination.

18. The method of using the non-rigid holder unit as defined in claim 17 further comprising the steps of:

inflating said component in a series of several sequential steps to a series of new predetermined pressures; and maintaining each of the new predetermined pressures for a preselected period of time during the examination.

19. The method of using the non-rigid holder unit as defined in claim 17 wherein a first predetermined pressure is approximately 30–80 mmHg.

20. The method of using the non-rigid holder unit as defined in claim 19 wherein said another predetermined pressure is approximately 2–5 mmHg.

* * * * *